(12) United States Patent
Hyodo et al.

(10) Patent No.: US 10,143,453 B2
(45) Date of Patent: Dec. 4, 2018

(54) SURGICAL TOOL AND MEDICAL MANIPULATOR

(71) Applicant: OLYMPUS CORPORATION, Tokyo (JP)

(72) Inventors: Ryoji Hyodo, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 530 days.

(21) Appl. No.: 14/607,322

(22) Filed: Jan. 28, 2015

(65) Prior Publication Data
US 2015/0142014 A1 May 21, 2015

Related U.S. Application Data

(63) Continuation of application No. PCT/JP2013/070337, filed on Jul. 26, 2013.

(30) Foreign Application Priority Data

Jul. 30, 2012 (JP) ................................. 2012-168353

(51) Int. Cl.
*A61B 17/00* (2006.01)
*A61B 34/37* (2016.01)
(Continued)

(52) U.S. Cl.
CPC ........ *A61B 17/00234* (2013.01); *A61B 34/30* (2016.02); *A61B 34/37* (2016.02);
(Continued)

(58) Field of Classification Search
CPC ... A61B 17/00234; A61B 34/30; A61B 34/37; A61B 2034/301; A61B 2017/2927; A61B 2017/2939; A61B 2017/2943
(Continued)

(56) References Cited

U.S. PATENT DOCUMENTS 6,206,903 B1 3/2001 Ramans
6,312,435 B1 11/2001 Wallace et al.
(Continued)

FOREIGN PATENT DOCUMENTS

JP 2006-116194 A 5/2006
JP 2006-247804 A 9/2006
(Continued)

OTHER PUBLICATIONS

International Search Report dated Sep. 10, 2013 issued in PCT/JP2013/070337.
(Continued)

*Primary Examiner* — Diane Yabut
*Assistant Examiner* — Erich Herbermann
(74) *Attorney, Agent, or Firm* — Scully, Scott, Murphy & Presser, P.C.

(57) ABSTRACT

In a surgical tool, the treatment tool piece operating joint includes a first operating rotation member which is coupled to the moving member and is rotated around a predetermined rotation center; a second operating rotation member which is coupled to the first operating rotation member so as to relatively rotate around a rotation center coaxial with the second bending rotary shaft in a rotation direction opposite to a rotation direction of the first operating rotation member or around a rotation center that is a position closer to the first bending rotary shaft than the second bending rotary shaft in a rotation direction opposite to a rotation direction of the first operating rotation member; and a link which converts a rotational force of the second operating rotation member into the operation of the treatment tool piece.

10 Claims, 7 Drawing Sheets

(51) Int. Cl.
*A61B 17/29* (2006.01)
*A61B 34/30* (2016.01)

(52) U.S. Cl.
CPC ............. *A61B 2017/2927* (2013.01); *A61B 2017/2939* (2013.01); *A61B 2017/2943* (2013.01); *A61B 2034/301* (2016.02)

(58) Field of Classification Search
USPC .......................................... 606/130
See application file for complete search history.

(56) References Cited

U.S. PATENT DOCUMENTS

| | | | |
|---|---|---|---|
| 2004/0199147 A1* | 10/2004 | Nishizawa | A61B 17/062 606/1 |
| 2006/0155262 A1* | 7/2006 | Kishi | A61B 34/70 606/1 |
| 2007/0208375 A1 | 9/2007 | Nishizawa et al. | |
| 2009/0112230 A1 | 4/2009 | Jinno | |
| 2011/0213346 A1* | 9/2011 | Morley | A61B 17/062 606/1 |
| 2014/0350570 A1 | 11/2014 | Lee | |

FOREIGN PATENT DOCUMENTS

| | | |
|---|---|---|
| JP | 2008-307310 A | 12/2008 |
| JP | 2009-107087 A | 5/2009 |
| JP | 2009-136684 A | 6/2009 |
| JP | 2011-530375 A | 12/2011 |
| JP | 2015-501697 A | 1/2015 |
| WO | 2010/019001 A2 | 2/2010 |
| WO | WO 2012/042949 A1 | 4/2012 |
| WO | WO 2012/073849 A1 | 6/2012 |

OTHER PUBLICATIONS

Japanese Office Action dated Jun. 21, 2016 in related Japanese Patent Application No. 2012-168351.
Extended Supplementary European Search Report dated Mar. 9, 2016 in related European Application No. 13 82 6486.6.

* cited by examiner

SURGICAL TOOL AND MEDICAL MANIPULATOR

TECHNICAL FIELD

The present invention relates to a surgical tool and a medical manipulator.

This application is a continuation application based on PCT/JP2013/070337, filed on Jul. 26, 2013, claiming priority based on Japanese Patent Application No. 2012-168353, filed on Jul. 30, 2012. The contents of both the Japanese Patent Application and the PCT Application are incorporated herein by reference.

BACKGROUND ART

In the related art, master slave type medical manipulators including a master manipulator manipulated by an operator and a slave manipulator that is operated on the basis of a signal issued from the master manipulator are known as medical manipulators. A surgical tool for performing treatment on a treatment target region through remote manipulation is attached to such a medical manipulator.

For example, a surgical tool having a double joint for changing the orientation of a treatment part at a distal end part of a longitudinal member is disclosed in U.S. Pat. No. 6,312,435. The double joint has two rotary shafts that extend in directions orthogonal to the longitudinal axis of the longitudinal member and are parallel to each other. One of the two rotary shafts is coupled to the longitudinal member, and the other of the two rotary shafts is coupled to the treatment part. Additionally, in the surgical tool described in U.S. patent application No. 6,312,435, the double joint is provided with a pair of openable and closable treatment tool pieces. As for the pair of treatment tool pieces provided at the surgical tool described in U.S. patent application No. 6,312,435, elongated driving members that independently operate the treatment tool pieces are connected to the treatment tool pieces, respectively.

SUMMARY OF THE INVENTION

A surgical tool related to a first aspect of the present invention is a surgical tool that performs treatment on a treatment target region. The surgical tool includes a tube-shaped longitudinal member which has a longitudinal axis; a bending double joint which is coupled to an end part of the longitudinal member in a direction of the longitudinal axis; a treatment tool piece which is coupled to the bending double joint and is operable; a treatment tool piece operating joint which is coupled to the treatment tool piece; and a moving member which is coupled to the treatment tool piece operating joint and is arranged along the longitudinal member. The bending double joint includes a first bending rotary shaft which is coupled to the longitudinal member; and a second bending rotary shaft which is parallel to the first bending rotary shaft and is coupled to the treatment part. The treatment tool piece operating joint includes a first operating rotation member which is coupled to the moving member and is rotated around a predetermined rotation center; a second operating rotation member which is coupled to the first operating rotation member so as to relatively rotate around a rotation center coaxial with the second bending rotary shaft in a rotation direction opposite to a rotation direction of the first operating rotation member or around a rotation center that is a position closer to the first bending rotary shaft than the second bending rotary shaft in a rotation direction opposite to a rotation direction of the first operating rotation member; and a link which converts a rotational force of the second operating rotation member into the operation of the treatment tool piece.

According to a second aspect of the present invention based on the above first aspect, the rotation center of the second operating rotation member may be coaxial with the second bending rotary shaft.

According to a third aspect of the present invention based on the above first aspect or the above second aspect, a rotatory shaft of the treatment tool piece may be coaxial with the rotation center of the second operating rotation member.

According to a fourth aspect of the present invention based on any one aspect of the above first aspect to the above third aspect, a rotatory shaft of the treatment tool piece may be coaxial with the second bending rotary shaft.

According to a fifth aspect of the present invention based on any one aspect of the above first aspect to the above fourth aspect, the rotation center of the first operating rotation member may be coaxial with the first bending rotary shaft.

According to a sixth aspect of the present invention based on any one aspect of the above first aspect to the above fifth aspect, the surgical tool may further include a pair of the treatment tool pieces, and the operation of the treatment tool piece may be the opening and closing of the pair of treatment tool pieces.

A medical manipulator related to a seventh aspect of the present invention includes the surgical tool according to any one aspect of the above first aspect to the above sixth aspect; a slave manipulator that has the surgical tool attached thereto and has at least one joint; and a master manipulator that issues a manipulation command for driving the joint of the slave manipulator.

DESCRIPTION OF EMBODIMENTS

Figure 1:
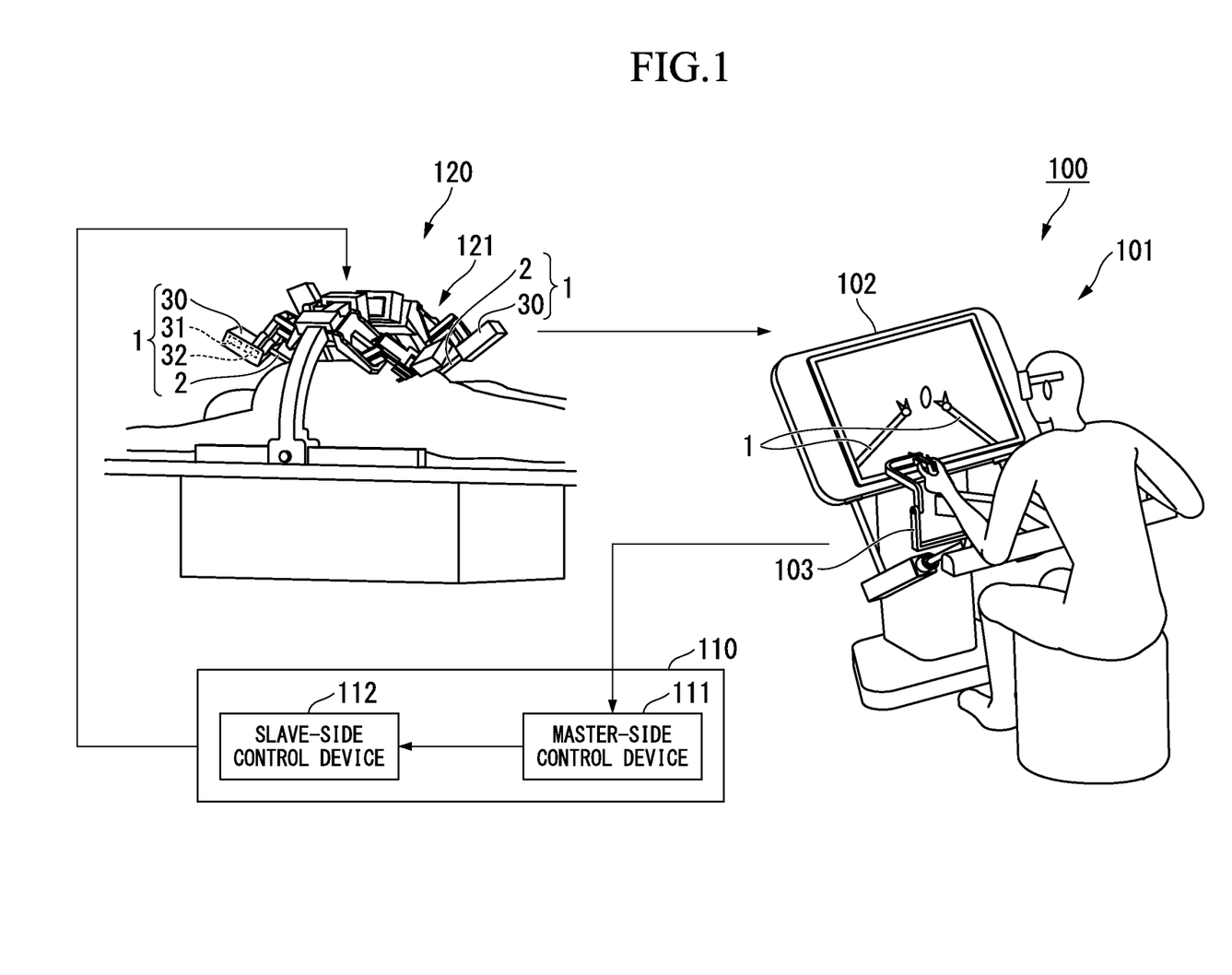
FIG. 1 is an overall view of a medical manipulator including a surgical tool of an embodiment of the present invention.
Figure 2:
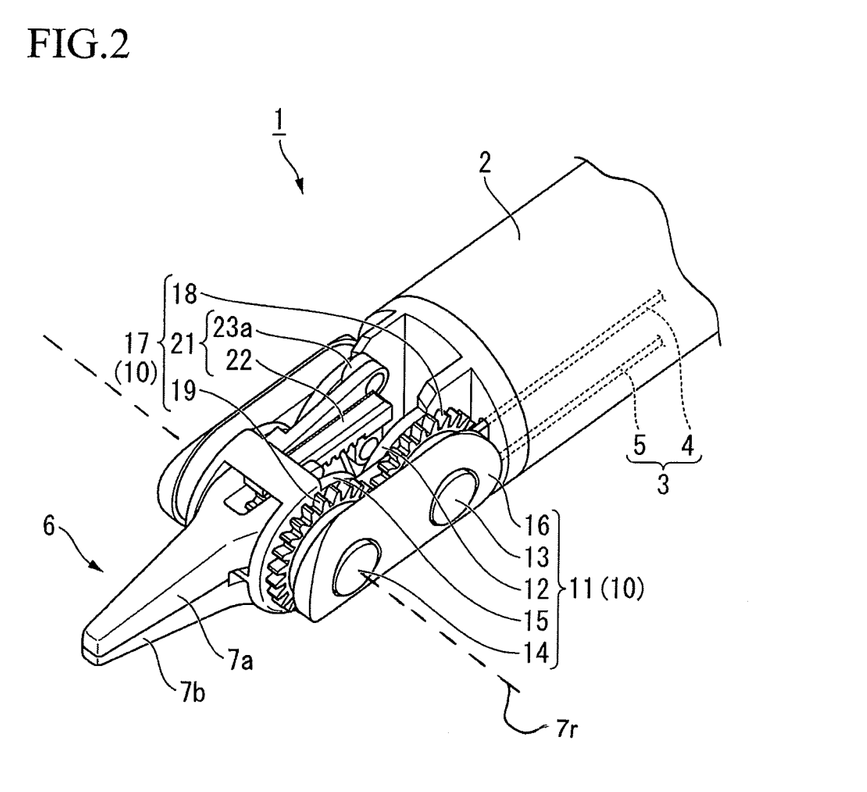
FIG. 2 is a perspective view showing a portion of the surgical tool.
Figure 3:
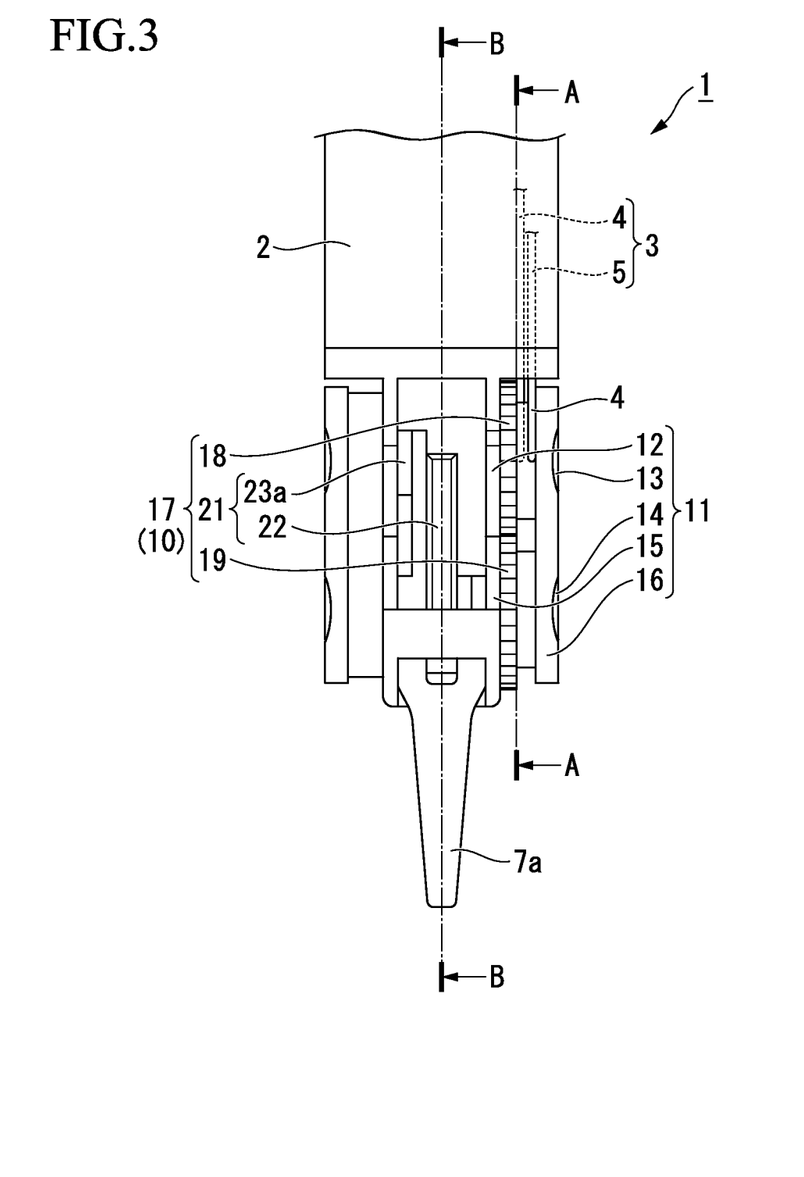
FIG. 3 is a plan view showing a portion of the surgical tool.
Figure 4:
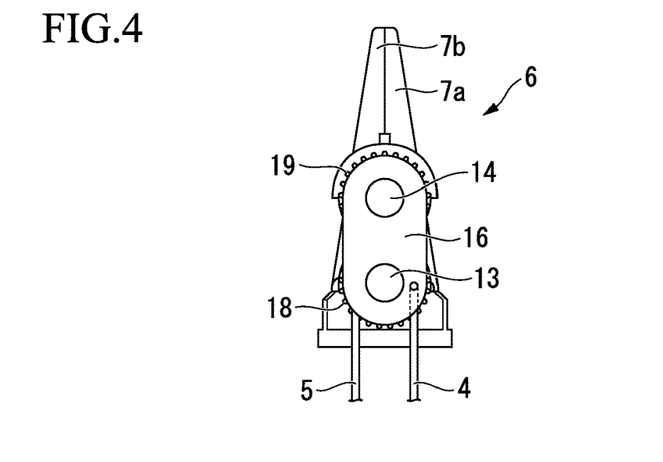
FIG. 4 is a side view showing a portion of the surgical tool.
Figure 5:
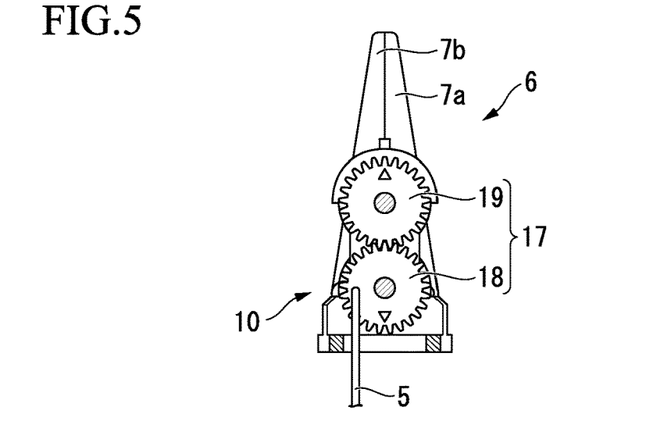
FIG. 5 is a cross-sectional view, taken along line A-A of FIG. 3, showing a portion of the surgical tool.
Figure 6:
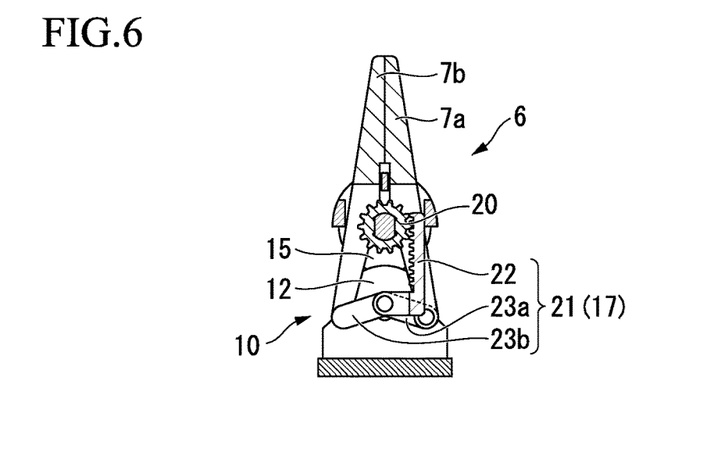
FIG. 6 is a cross-sectional view, taken along line B-B of FIG. 3, showing a portion of the surgical tool.

A surgical tool and a medical manipulator of an embodiment of the present invention will be described. FIG. 1 is an overall view of the medical manipulator including the surgical tool of the present embodiment. FIG. 2 is a perspective view showing a portion of the surgical tool. FIG. 3 is a plan view showing a portion of the surgical tool. FIG. 4 is a side view showing a portion of the surgical tool. FIG. 5 is a cross-sectional view taken along line A-A of FIG. 3. FIG. 6 is a cross-sectional view taken along line B-B of FIG. 3.

As shown in FIG. 1, a surgical tool 1 is attached to a medical manipulator 100, as a portion of the medical manipulator 100.

First, the configuration of the medical manipulator 100 of the present embodiment will be described. The medical manipulator 100 includes a master manipulator 101, a control device 110, and a slave manipulator 120.

The master manipulator 101 functions as a master that transmits a surgeon's manipulation motion to the slave manipulator 120, and includes a master display part 102, such as a liquid crystal display device, and a manipulation part 103 that is gripped and manipulated by a surgeon. A manipulation performed on the manipulation part 103 of the master manipulator 101 is input to the control device 110.

The control device 110 has a master-side control device 111 that receives the input from the master manipulator 101, and a slave-side control device 112 that outputs a driving signal to the slave manipulator 120.

In the master-side control device 111, a manipulation command for operating the slave manipulator 120 is generated on the basis of the input from the master manipulator 101, and is output to the slave-side control device 112.

In the slave-side control device 112, a driving signal for driving the slave manipulator 120 is generated on the basis of the manipulation command issued from the master-side control device 111, and is output to the slave manipulator 120.

The slave manipulator 120 has a slave arm 121 that operates according to the driving signal from the slave-side control device 112, and the surgical tool 1 of the present embodiment is attached to the slave arm 121. A treatment instrument, an endoscope apparatus, or the like for performing a surgical operation in addition to the surgical tool 1 of the present embodiment can be attached to the slave manipulator 120.

Next, the configuration of the surgical tool 1 will be described.

The surgical tool 1 shown in FIG. 1 is a medical instrument for performing a treatment on a treatment target region. As shown in FIGS. 1 and 2, the surgical tool 1 includes an longitudinal member 2, a treatment part 6 that is coupled to a first end part (end part) of the longitudinal member 2 via a joint 10, and a driving control part 30 that is provided at a second end part of the longitudinal member 2. Hereinafter, description will be described while the side of the surgical tool 1 where the treatment part 6 is provided is referred to as a distal side and the side of the surgical tool 1 where the driving control part 30 is provided is referred to as a proximal side.

The longitudinal member 2 is a tubular member having a longitudinal axis. The longitudinal member 2 may be flexible or rigid according to the configuration of the slave arm 121 serving as an attachment target. In the present embodiment, an example in which the longitudinal member 2 is rigid is shown.

As shown in FIGS. 2 and 3, a connecting rod 3 for operating the treatment part 6 is disposed inside the longitudinal member 2. A connecting rod 3 has a bending rod 4 and an opening and closing rod 5 (moving member).

A first end of the bending rod 4 is coupled to a bending double joint 11 to be described below, and a second end of the bending rod 4 is coupled to the driving control part 30.

A first end of the opening and closing rod 5 is coupled to an opening and closing joint 17 to be described below, and a second end of the opening and closing rod 5 is coupled to the driving control part 30.

As shown in FIGS. 2 and 3, the treatment part 6 is provided in order to perform a treatment on a treatment target region. In the present embodiment, the treatment part 6 has a pair of openable and closable forceps pieces (treatment tool pieces) 7a and 7b, and the surgical tool 1 is forceps. The pair of forceps pieces 7a and 7b are coupled together by a shaft-shaped member (not shown) serving as a rotary shaft of each of the forceps pieces 7a and 7b. In the present embodiment, a rotation center in the shaft-shaped member is coaxial with the rotation center of a second bending rotary shaft 14 to be described below.

The joint 10 that couples the longitudinal member 2 and the treatment part 6 together has the bending double joint 11 for bending the treatment part 6 with respect to the longitudinal member 2, and the opening and closing joint 17 (treatment tool piece operating joint) for opening and closing the pair of forceps pieces 7a and 7b.

The bending double joint 11 has a first fitting teeth part 12 that is fixed to a distal end of the longitudinal member 2, a first bending rotary shaft 13 that is coupled to the distal end of the longitudinal member 2, the second bending rotary shaft 14 that extends parallel to the first bending rotary shaft 13 and is coupled to the treatment part 6, a second fitting teeth part 15 that comes into rolling contact with the first fitting teeth part 12 fixed to the treatment part 6, and a body part 16 that rotatably holds the first bending rotary shaft 13 and the second bending rotary shaft 14, respectively.

The first fitting teeth part 12 has gear-like teeth on a circumference centered on the rotation center of the first bending rotary shaft 13. Additionally, the second fitting teeth part 15 has gear-like gear teeth on a circumference centered on the rotation center of the second bending rotary shaft 14, and meshes with the first fitting teeth part 12.

The first fitting teeth part 12 and the second fitting teeth part 15 have the gear teeth on the circumferences of which radii are equal to each other, and the ratio of the teeth is set in the relationship of 1:1.

The second fitting teeth part 15 is movable while rotating along the circumference in the first fitting teeth part 12. In addition, the plate-shaped members of which outer peripheral portions relatively rotate in contact with each other with a frictional force may be provided instead of the first fitting teeth part 12 and the second fitting teeth part 15.

Although a configuration in which the first fitting teeth part 12 and the second fitting teeth part 15 are brought into frictional contact with each other by the gear meshing is shown in the present embodiment, the present invention is not necessarily limited to a configuration in which the teeth parts are brought into frictional contact with each other by the gear meshing. For example, a mechanism in which two rotary bodies can be rotationally rolled without any slip therebetween like a configuration or the like in which two rubber rollers (a frictional force is large) with no gear meshing that are brought into frictional contact with each other can be used instead of the frictional contact caused by the gear meshing.

Both the first bending rotary shaft 13 and the second bending rotary shaft 14 are shafts of which the rotation centers extend in directions orthogonal to an extension line of a longitudinal axis of the longitudinal member 2.

Figure 7:
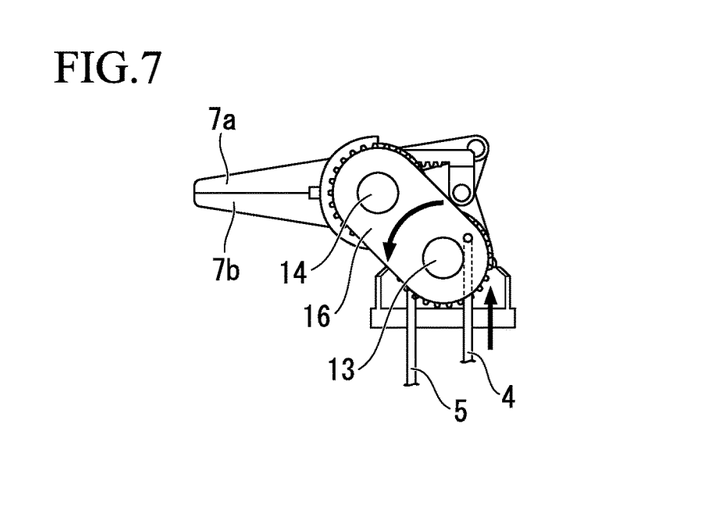
FIG. 7 is a view for describing the action of the surgical tool.

The body part 16 keeps the distance between the first fitting teeth part 12 and the second fitting teeth part 15 constant. As shown in FIGS. 3 and 4, the bending rod 4 of the connecting rod 3 is connected to the position of the body part 16 other than the first bending rotary shaft 13. By advancing and retracting the bending rod 4 in the direction of the longitudinal axis of the longitudinal member 2, the body part 16 rotates around the first bending rotary shaft 13. Accordingly, the second bending rotary shaft 14 is turned with the first bending rotary shaft 13 as a turning center (refer to FIG. 7).

As shown in FIGS. 3, 5, and 6, the opening and closing joint 17 has a first gear 18 (a first rotation member for operating a treatment tool piece), a second gear 19 (a second rotation member for operating a treatment tool piece), and a link 21.

The first gear 18 is a gear that is coupled to the opening and closing rod 5 and rotated around a predetermined rotation center. In the present embodiment, the predetermined rotation center in the first gear 18 is coaxial with the rotation center of the first bending rotary shaft 13 in the bending double joint 11. Additionally, in the present embodiment, the second gear 19 is a gear that meshes with the first gear 18 to be thereby coupled to the first gear 18 and relatively rotates in a direction opposite to the first gear 18 around a rotation center that is coaxial with the second bending rotary shaft 14.

The first gear 18 and the second gear 19 are gears of which the radii are equal to each other. Additionally, the second gear 19 is formed with a pinion 20 coupled to the link 21.

As shown in FIG. 6, the link 21 converts the rotational force of the second gear 19 into the opening and closing operation of the forceps. The link 21 has a rack 22 that meshes with the pinion 20, and link elements 23a and 23b that are coupled to the rack 22. The rack 22 advances and retracts as the pinion 20 rotates. The link elements 23a and 23b convert the advancing and retracting movement of the rack 22 into the rotational movement of the respective forceps pieces 7a and 7b. In the present embodiment, the link 21 constitutes a toggle mechanism, and is configured so that the gripping force of the forceps pieces 7a and 7b increases exponentially as the respective forceps pieces 7a and 7b move in closing directions.

The driving control part 30 shown in FIG. 1 has an actuator 31 that advances and retracts the connecting rod 3 (refer to FIG. 2) in the direction of the longitudinal axis of the longitudinal member 2, and a detector 32 that detects the operation amount of the actuator 31. The driving control part 30 operates according to the driving signal output from the slave-side control device 112. The detector 32 detects the operation amount of the actuator 31 to output the operation amount to the slave-side control device 112. Accordingly, the operation of the actuator 31 in the driving control part 30 is feedback-controlled.

Next, the actions of the surgical tool 1 and the medical manipulator 100 of the present embodiment will be described focusing on the operation principle and action of the surgical tool 1. FIGS. 7 to 12 are views for describing the action of the surgical tool 1.

As shown in FIGS. 2 and 3, the surgical tool 1 has a configuration in which the treatment part 6 and the longitudinal member 2 are coupled to the bending double joint 11 and the opening and closing joint 17. The bending double joint 11 can be operated by the advancing and retracting operation of the bending rod 4 by the actuator 31. Additionally, the opening and closing joint 17 can be operated independently from the bending double joint 11 by the advancing and retracting operation of the opening and closing rod 5 by the actuator 31.

Figure 8:
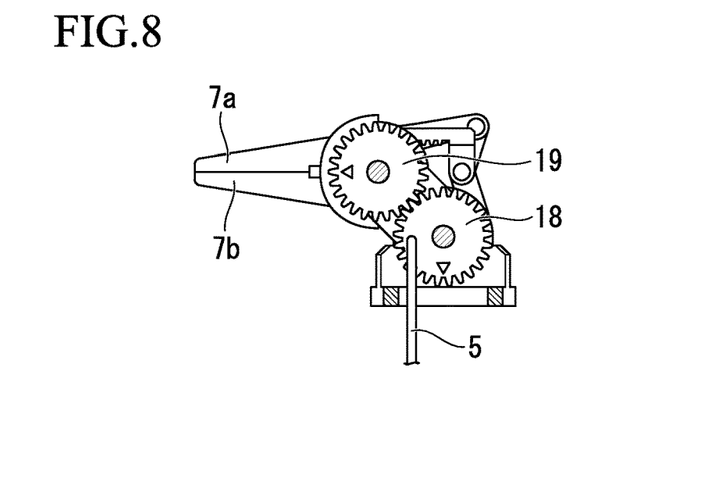
FIG. 8 is a view for describing the action of the surgical tool.

If the opening and closing rod 5 is not advanced and retracted but the bending rod 4 is advanced and retracted as shown in FIGS. 5 and 8, the second bending rotary shaft 14 rotates with the first bending rotary shaft 13 as a turning center. In this case, since the second fitting teeth part 15 meshes with the first fitting teeth part 12 provided at the bending double joint 11, the second fitting teeth part 15 rotates with the second bending rotary shaft 14 as a rotation center. In this case, the first gear 18 does not rotate but the body part 16 of the bending double joint 11 rotates around the first bending rotary shaft 13. As the second fitting teeth part 15 rotates around the second bending rotary shaft 14 while the second bending rotary shaft 14 turns with the first bending rotary shaft 13 as a turning center, the orientation of the pair of forceps pieces 7a and 7b in the treatment part 6 changes.

In this case, in the bending double joint 11, the body part 16 is moved at an angle according to the ratio of the radius of the first fitting teeth part 12 and the radius of the second fitting teeth part 15.

For example, as shown in FIG. 4, if the radius of the first fitting teeth part 12 is defined as r1, the radius of the second fitting teeth part 15 is defined as r2, the rotational angle of the body part 16 is defined as θ, and the rotational angle of the treatment part 6 is defined as φ, $$r2(\phi-\theta)=r1\theta \tag{1}$$

$$\phi=\{(r1+r2)/r2\}\theta \tag{2}$$

For example, when the ratio of the radius r1 of the first fitting teeth part 12 and the radius r2 of the second fitting teeth part 15 is 1:1 as in the present embodiment (r1=r2), the following is satisfied.

$$\phi=2\theta$$

Accordingly, if the body part 16 is moved by 45 degrees around the first bending rotary shaft 13, the second fitting teeth part 15 provided on the treatment part 6 side inclines by 90 degrees with respect to the first fitting teeth part 12. That is, since the bending double joint 11 serves as a speed increasing mechanism, the angular movement amount of the body part 16 can be lessened with respect to an intended angular movement amount of the treatment part 6.

Figure 9:
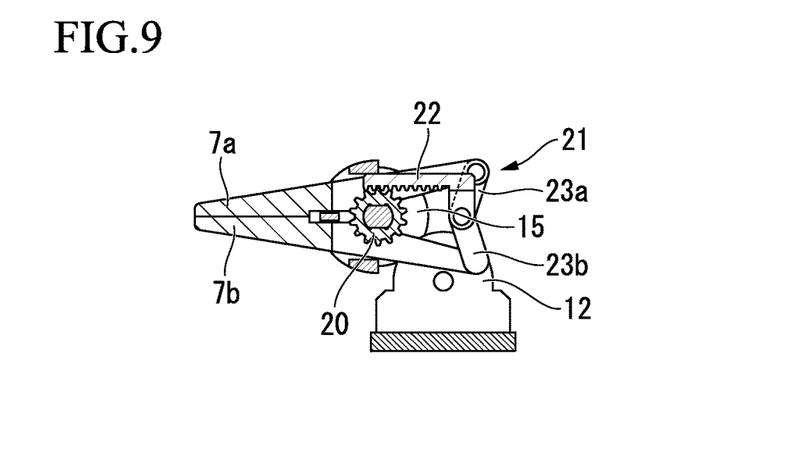
FIG. 9 is a view for describing the action of the surgical tool.
Figure 10:
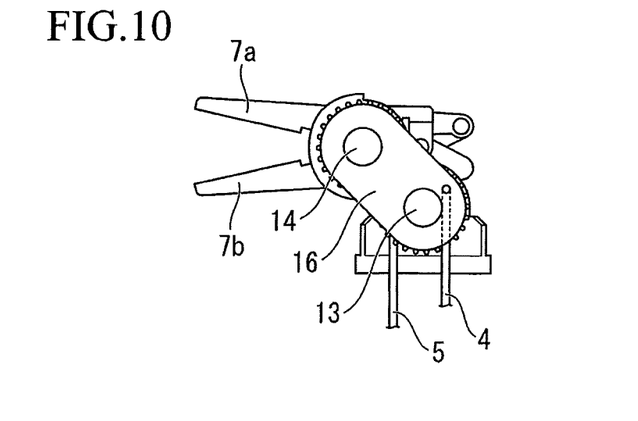
FIG. 10 is a view for describing the action of the surgical tool.

Here, as shown in FIGS. 6 and 9, since the orientations of the pinion 20 and the pair of forceps pieces 7a and 7b change integrally, the rotational operation of the pinion 20 such that the pair of forceps pieces 7a and 7b are opened and closed does not occur. Accordingly, an opened/closed state does not change before and after the orientation of the pair of forceps pieces 7a and 7b is changed.

Figure 11:
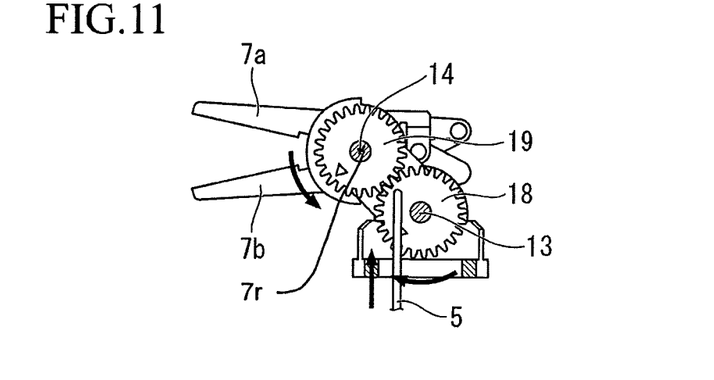
FIG. 11 is a view for describing the action of the surgical tool.
Figure 12:
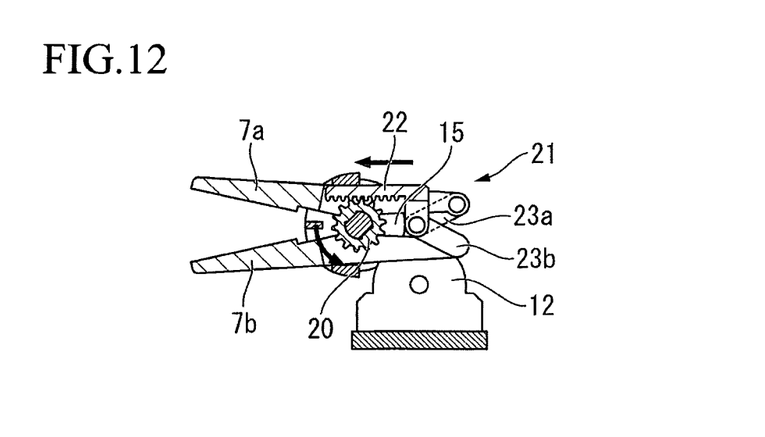
FIG. 12 is a view for describing the action of the surgical tool.

Next, if the opening and closing rod 5 is advanced and retracted as shown in FIGS. 8 and 11, the first gear 18 connected to the opening and closing rod 5 rotates, and the second gear 19 that meshes with the first gear 18 rotates. The second gear 19 rotates the pinion 20 as shown in FIGS. 9 and 12. As the pinion 20 rotates, the rack 22 advances and retracts, and the pair of forceps pieces open and close.

A configuration in which a rotary axis for changing the orientation of the forceps pieces 7a and 7b is provided on the distal side of the double joint 10 is known in the related art. As compared to such a configuration, the surgical tool 1 of the present embodiment has a configuration in which the rotary axis on the distal side in the double joint 10 coincides with the rotary axis 7r for changing the orientation of the forceps pieces 7a and 7b. Accordingly, the surgical tool 1 can be miniaturized compared to the related art, and a minimum radius that is required to change the orientation of the forceps pieces 7a and 7b can be made small.

In this way, according to the treatment tool of the present embodiment, the forceps pieces 7a and 7b can be directed to a desired orientation within a region narrower than that of the related art, and it becomes easy to do minute work on a treatment target region.

Additionally, the advancing and retracting movement of the opening and closing rod 5 is converted into the opening and closing operation of the forceps pieces 7a and 7b by the link 21. Accordingly, since the operations of the respective forceps pieces 7a and 7b interlock with each other, the cooperative operation when the forceps pieces 7a and 7b are opened and closed is unnecessary. For this reason, the control of opening and closing the forceps pieces 7a and 7b can be easily performed by the control of the advancing and retracting movement amount of the opening and closing rod 5.

Additionally, the medical manipulator 100 to which the surgical tool 1 of the present embodiment is attached to the slave arm 121 can favorably perform a treatment on a treatment target region even in a space narrower than that of the related art.

Although the embodiment of the present invention has been described above in detail with reference to the drawings, the specific configuration of the present invention is not limited to the embodiment, and design changes or the like are also included without departing from the scope of the present invention.

Figure 13:
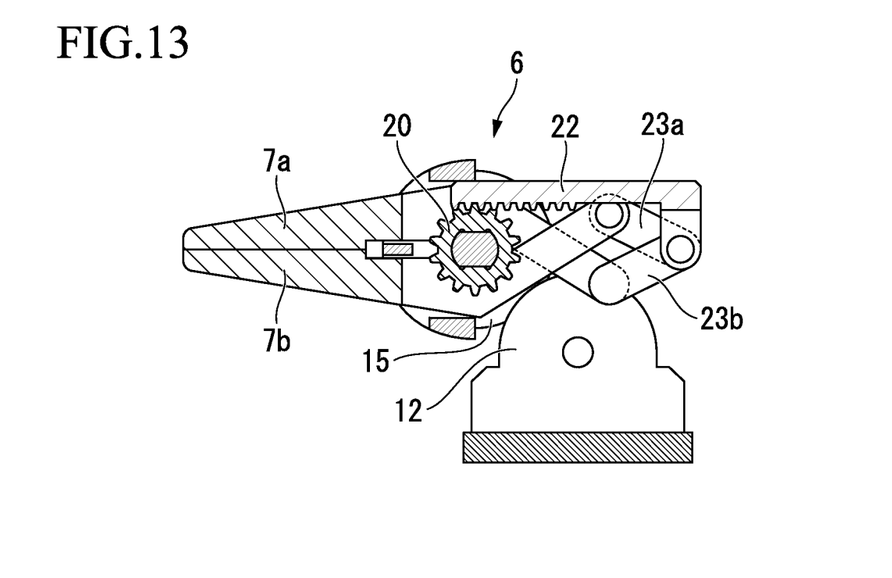
FIG. 13 is a view showing an example of design changes of the surgical tool, and is a view showing the same cross-section as line B-B of FIG. 3.
Figure 14:
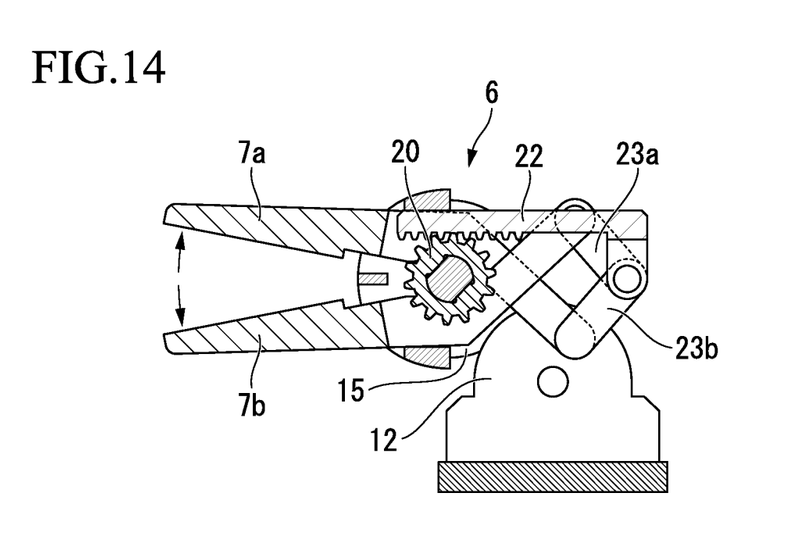
FIG. 14 is a view for describing the action of a treatment part in the design changes shown in FIG. 13.

For example, as shown in FIGS. 13 and 14, a link mechanism that operates in the shape of a pantagraph can also be adopted as a combination of the forceps pieces 7a and 7b and the link elements 23a and 23b. The forceps pieces 7a and 7b can be opened and closed even in such a configuration.

Additionally, as an example of another design change, for example, the second gear 19 may rotate with a position closer to the first bending rotary shaft 13 than the second bending rotary shaft 14 as a rotation center, regarding the rotation center of each of the second bending rotary shaft 14 and the second gear 19.

Additionally, an opening and closing rotary axis 7r of the forceps pieces 7a and 7b may not be coaxial with the second bending rotary shaft 14 or the rotation center of the second gear 19.

Additionally, although the operation of opening and closing the forceps pieces 7a and 7b that are the pair of treatment tool pieces has been described as an example of the operation of the treatment tool pieces in the above-described embodiment, the present invention is not limited to this. For example, the above operation may be the operation of bending (rotating) one treatment tool piece or the operation of advancing and retracting one treatment tool piece in a predetermined direction.

Additionally, the treatment tool pieces may be medical instruments other than the forceps pieces.

Additionally, a wire having flexibility may be provided instead of the connecting rod 3 described in the above-described embodiment. Additionally, the longitudinal member 2 of the surgical tool 1 may be flexible.

In addition, design changes or the like to the above specific configurations are not limited to the above matters.

The invention claimed is:

1. A surgical tool comprising:
   a longitudinal member;
   a bending double joint coupled to an end part of the longitudinal member so as to be actuated by a first actuating member; and
   a treatment part coupled to the bending double joint, the treatment part being configured to perform a treatment on a target region so as to be actuated by a second actuating member;
   wherein the bending double joint comprises:
      a first fitting teeth part fixed to a distal end of the longitudinal member, the first fitting teeth part configured to rotate about a first axis;
      a second fitting teeth part fixed to the treatment part and comes into rolling contact with the first fitting teeth part, the second fitting teeth part being configured to rotate about a second axis, the second axis being parallel to the first axis; and
      a body part rotatably coupled to both the first axis and the second axis, and
   wherein the treatment part comprises:
      a first operating rotation member configured to be rotated about the first axis by the second actuating member;
      a second operating rotation member configured to be rotated about the second axis by rotating the first operating rotation member; and
      a link configured to actuate the treatment part by converting a rotational force caused by rotating the second operating rotation member, wherein the link comprises:
         a rack configured to be moved by meshing with a pinion when the pinion is rotated; and
         a link mechanism coupled to the rack, the link mechanism being configured to actuate the treatment part by converting a force caused by moving the rack.

2. The surgical tool according to claim 1, wherein the treatment part comprising a pair of jaws configured to be opened or closed by the link.

3. The surgical tool according to claim 1, wherein the first operating rotation member comprising a first gear, and the second operating rotation member comprising a second gear, the second gear being configured to be rotated about the second axis by meshing with the first gear when the first gear is rotated.

4. The surgical tool according to claim 1, wherein the link mechanism is a toggle mechanism.

5. The surgical tool according to claim 1, wherein the link mechanism is a pantagraph mechanism.

6. A medical manipulator comprising:
   a slave manipulator comprising the surgical tool according to claim 1;
   a master manipulator configured to generate a command so as to operate the slave manipulator;
   an actuator configured to actuate the first actuating member or the second actuating member; and
   a controller configured to control the actuator by the command.

7. The medical manipulator according to claim 6, further comprising a detector configured to detect an operation amount of the actuator, wherein the controller is configured to control the actuator based on the detected operation amount of the actuator.

8. The medical manipulator according to claim 6, wherein the first operating rotation member comprising a first gear, and the second operating rotation member comprising a second gear, the second gear configured to be rotated about the second axis by meshing with the first gear rotated.

9. The medical manipulator according to claim 6, wherein the link mechanism is a toggle mechanism.

10. The medical manipulator according to claim 6, wherein the link mechanism is a pantagraph mechanism.

* * * * *